United States Patent [19]

Kato

[11] Patent Number: 5,162,651
[45] Date of Patent: Nov. 10, 1992

[54] MASS SPECTROMETER

[75] Inventor: Yoshiaki Kato, Mito, Japan

[73] Assignee: Hitachi, Ltd., Tokyo, Japan

[21] Appl. No.: 783,245

[22] Filed: Oct. 28, 1991

[30] Foreign Application Priority Data

Oct. 26, 1990 [JP] Japan .................................. 2-289628

[51] Int. Cl.⁵ ............................................. H01J 49/04
[52] U.S. Cl. ..................... 250/288; 250/281
[58] Field of Search .................... 250/288, 288 A, 281

[56] References Cited

U.S. PATENT DOCUMENTS 4,358,302 11/1982 Dahneke ............................. 250/288
4,977,785 12/1990 Willoughby et al. ............... 250/288

OTHER PUBLICATIONS

Huang et al., Analytical Chemistry, vol. 62, No. 13, Jul. 1, 1990, pp. 713A-725A.
Bruins et al., Analytical Chemistry, vol. 59, No. 22, Nov. 15, 1987, pp. 2642-2646.

Primary Examiner—Jack I. Berman
Attorney, Agent, or Firm—Antonelli, Terry, Stout & Kraus

[57] ABSTRACT

A mass spectrometer comprising an ion sprayer having a first tube and a second tube outside of the first tube, wherein nebulizing gas is emitted from the first tube and liquid sample is emitted from a space between the first tube and the second tube, an counter electrode for sampling ions having a hole thereon opposite to an outlet of the nebulized gas in the ion sprayer, wherein a high voltage is applied between the ion spray device and the electrode so as to sample the ions from the hole, and an means for sorting a mass of the ions sampled through the hole.

18 Claims, 3 Drawing Sheets

MASS SPECTROMETER

BACKGROUND OF THE INVENTION

The present invention relates to a mass spectrometer and more particularly to the mass spectrometer having an ion sprayer which effectively forms concentrated ion beam.

In the general mass spectrometry for analyzing polar molecules dissolved in liquid, a combined liquid chromatography/mass spectrometry (herein after called LC/MS) with a sprayer is widely used. In such LC/MS, the liquid sample is nebulized and ionized simultaneously under an atmospheric pressure based on an electrospray method or a pneumatically assisted electrospray method, and the ionized polar molecules are sampled and introduced into the analyzing means in the mass spectrometer.

The sprayer in these LC/MS has a nozzle for ionizing the sample which consists of a first capillary tube and a second capillary tube outside of the first capillary tube. The liquid sample passes through the first capillary tube and is emitted out from an end of the first capillary tube and at the same time nebulizing gas is emitted out from an end space between the first capillary tube and a second capillary tube so as to nebulize the liquid sample as small droplets. As an end electrode having hole is obtained opposite to the end portion of the nozzle and a high voltage is applied between the nozzle and the counter electrode from the end of the nozzle, the nebulized sample compounds are ionized as many ions and these ions are moved towards the counter electrode. Some of the ions are passed through the hole of counter electrode so as to be sampled and be introduced to the analyzing means for sorting respective masses of the ions.

In the general LC/MS, the ions are dispersed in front of the electrode and a maximum portion of the ion density usually forms a ring on the electrode. Therefore, the hole of the electrode is disposed on the maximum portion in order to sample the ions. But, as the ions are sampled from the only one part of the ring of the ions, the sampling efficiency is not so high.

Examples of such conventional LC/MS relating the electrospray method or the pneumatically assisted electrospray method are disclosed as follows; (1) "Ion Spray Interface for Combined Liquid Chromatography/Atmospheric Pressure Ionization Mass Spectrometry", Analytical Chemistry, Vol. 59, No. 22, Nov. 15, 1987, pp. 2642–2646

(2) "Atmospheric Pressure Ionization Mass Spectrometry", Analytical Chemistry, Vol. 62, No. 13, Jul. 1, 1990, pp. 713A–725A

SUMMARY OF THE INVENTION

The present invention has been accomplished to overcome the above-mentioned problem of the conventional mass spectrometry.

An object of present invention is to provide a mass spectrometer which is improved the sampling efficiency of ions.

In order to improve the ion sampling efficiency of the mass spectrometry having a first tube, a second tube outside of the first tube as the ion sprayer and an counter electrode having a hole from which ions are sampled wherein a high DC voltage is applied between the first or the second tube and the counter electrode, nebulizing gas is emitted from an end portion of the first tube and liquid sample is emitted from an end space between the first tube and the second tube.

Furthermore, the ion sprayer of the mass spectrometry in the present invention has an outer tube outside of the second tube, and other gas is emitted from an end space between the second tube and the outer tube.

As the ion sprayer is constructed as stated above, density of the ions becomes maximum at one point and the hole of counter electrode of the ion sprayer is positioned at the one point so as to effectively sample the ions.

Furthermore in the present invention, the end portion of the first tube is retired from the end of the second tube and the end portion of the second tube is more protruded than that of the outer tube. On the counter electrode, a convex portion which is protruded towards the sprayer nozzle is provided and the hole is positioned on the top of the convex portion in order to gather more ions at the one point.

Furthermore, flow rates and temperatures of the nebulizing gas and makeup gas are suitably adjusted.

DETAILED DESCRIPTION OF THE PREFERRED EMBODIMENTS

Figure 1:
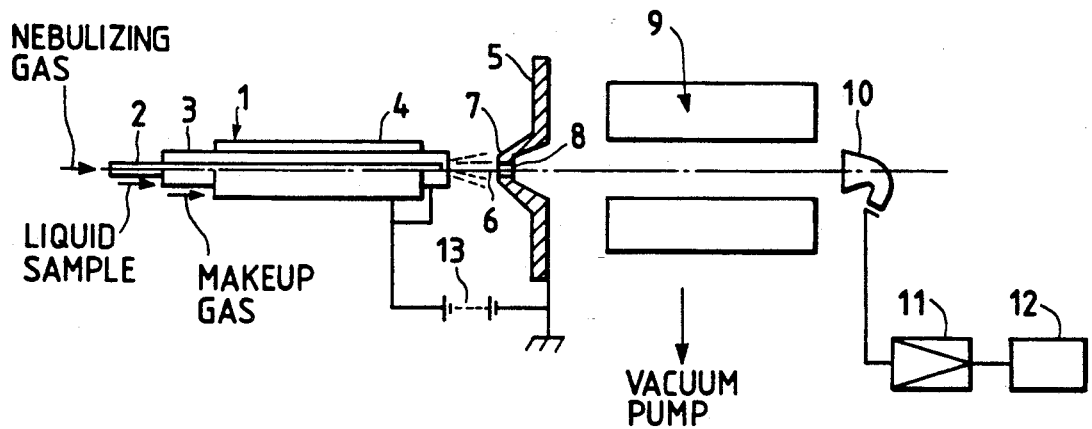
FIG. 1 is a schematic view of a total structure of a mass spectrometer in the present invention.

In a schematic view of a total structure of a mass spectrometer shown in FIG. 1, numeral 1 denotes a sprayer, wherein the sprayer 1 consists of the first inner tube 2 disposed in the most inner side, a second inner tube 3 distributed coaxially outside of the first inner tube 2 and an outer tube 4 distributed outside of the second inner tube 2, all of which are disposed coaxially so as to have a same central axis.

An end portion of the sprayer forms a nozzle and the nozzle faces an counter electrode 5. The end portion of the second inner tube 3 is protruded 5 to 10 mm more than the end portion of the outer tube towards the counter electrode 5, and the end portion of the first inner tube 2 is retired 1 to 5 mm from the end of the second inner tubes. A convex portion 7 such as a cone is formed on the counter electrode 5 and opposite to the nozzle of the sprayer 1. The convex portion 7 is protruded towards the nozzle. On a top of the convex portion 7, a small ion sampling hole 8 is formed and is disposed on the central axis 6 of the sprayer 1.

Outside of the electrode 5, that is, nozzle side of the electrode 5, is kept in an atmospheric pressure or in a lower pressure than the atmospheric pressure, and inside of the counter electrode 5, that is the mass spectrometer side, is kept in a vacuum state by a vacuum pump not shown in the figure. In the inside of the electrode 5, quadrupole mass filter 9 and ion detector 10. The detector 10 detects ions sampled through the counter electrode 5 and feeds an electric signal to an amplifier 11. The electric signal from the amplifier 11 is transmitted to a data processing system 12.

A DC voltage source 13 which supplies a high DC voltage is connected to the counter electrode 5 and the second inner tube 3, and applies the DC voltage between the counter electrode 5 and the second inner tube 3. The second inner tube 3 is positively or negatively charged against the counter electrode 5 which is connected to the ground. The first and the second inner tubes are made of stainless steel and the outer tube is made of Teflon resin or stainless steel. The first inner tube 2 is connected to a positive or negative terminal of the DC voltage source 13 and in the case the outer tube 4 is made of the stainless steel, the outer tube 4 is connected the positive or negative terminal too. The polarity of the applied high voltage on the sprayer tube depends on the polarity of ions emitted from the nozzle.

In such a structure stated above, liquid sample eluted from a liquid chromatograph not shown in figure flows between the first inner tube 2 and the second inner tube 3 so as to reach the nozzle of the sprayer 1. Nebulizing gas flows in the first inner tube 2 and makeup gas is flown between the second inner tube 3 and the outer tube 4. As the nebulizing gas and the makeup gas, inert gas such as Nitrogen gas for example is used.

Figure 2:
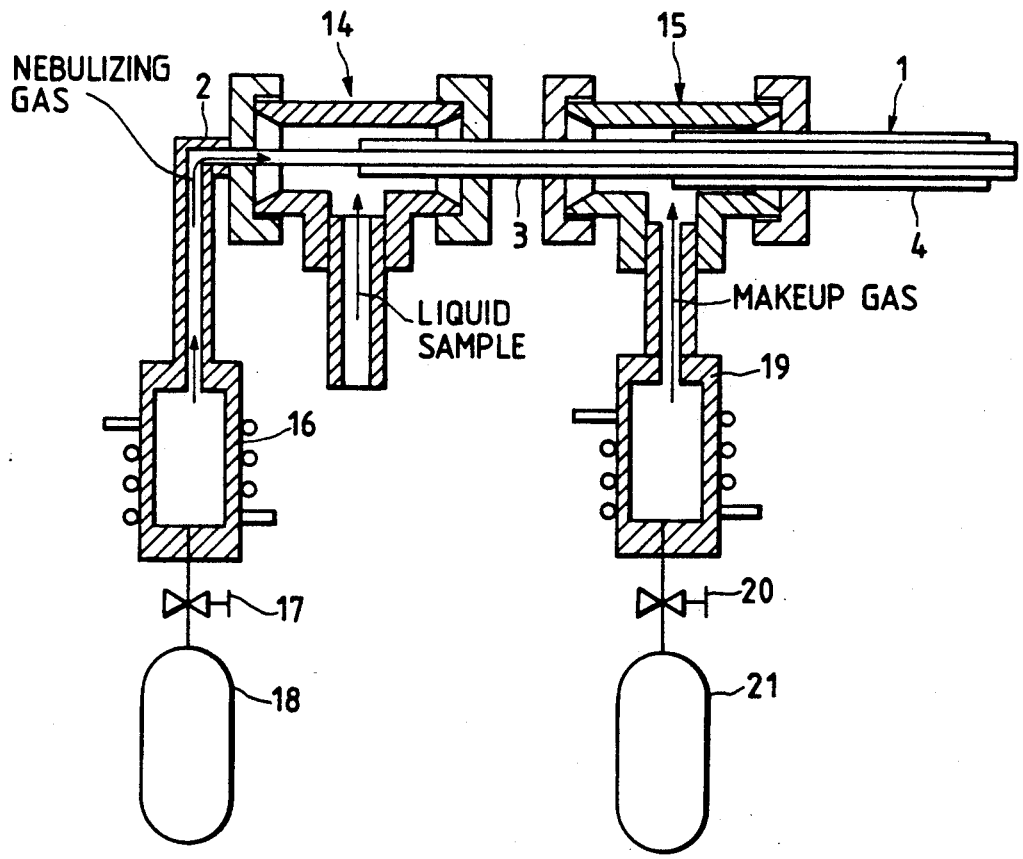
FIG. 2 is a sectional view of a sprayer in the present invention.

In FIG. 2, more detailed figure of the sprayer 1 is shown. The first inner tube 2 is disposed through a first tee 14 and a gas inlet of the first inner tube 2 is installed at an outside of the tee 14. A sample inlet of the second inner tube 3 is disposed inside of the tee 14. The first inner tube 2 and the second inner tube 3 are commonly installed through a second tee 15 and a gas inlet of the outer tube 4 is disposed inside of the second tee 15.

The liquid sample from the liquid chromatograph is supplied into the inlet of the second inner tube 3 which is inside of the first tee 14 and is transmitted through a space between the first inner tube 2 and the second inner tube 3 so as to reach the nozzle of the sprayer 1. The nebulizing gas stored in a gas cylinder 18 is transmitted through a control valve 17 and a heater 16, and is supplied to the inlet of the first inner tube 2. in the same way, the makeup gas stored in a gas cylinder 21 is transmitted through a control valve 20 and a heater 19, and is supplied to the inlet of the outer tube 4.

Flow rate of the nebulizing gas in the first inner tube 2 is controlled by the control valve 17 and temperature of the nebulizing gas in the first inner tube 2 is controlled by the heater 16 while the nebulizing gas passes through the heater 16. In the same way, flow rate of the makeup gas in the outer tube 4 is controlled by the control valve 20 and temperature of the makeup gas in the outer tube 4 is controlled by the heater 19 while the makeup gas passes through the heater 19.

The liquid sample reached the nozzle of the sprayer 1 is ejected into an area between the nozzle and the counter electrode 5 which is added a high DC voltage and is under the atmospheric pressure or a little lower pressure than the atmospheric pressure so as to be changed to be charged nebulizing sample and finally to be ions as ionized polar molecules.

Figure 3:
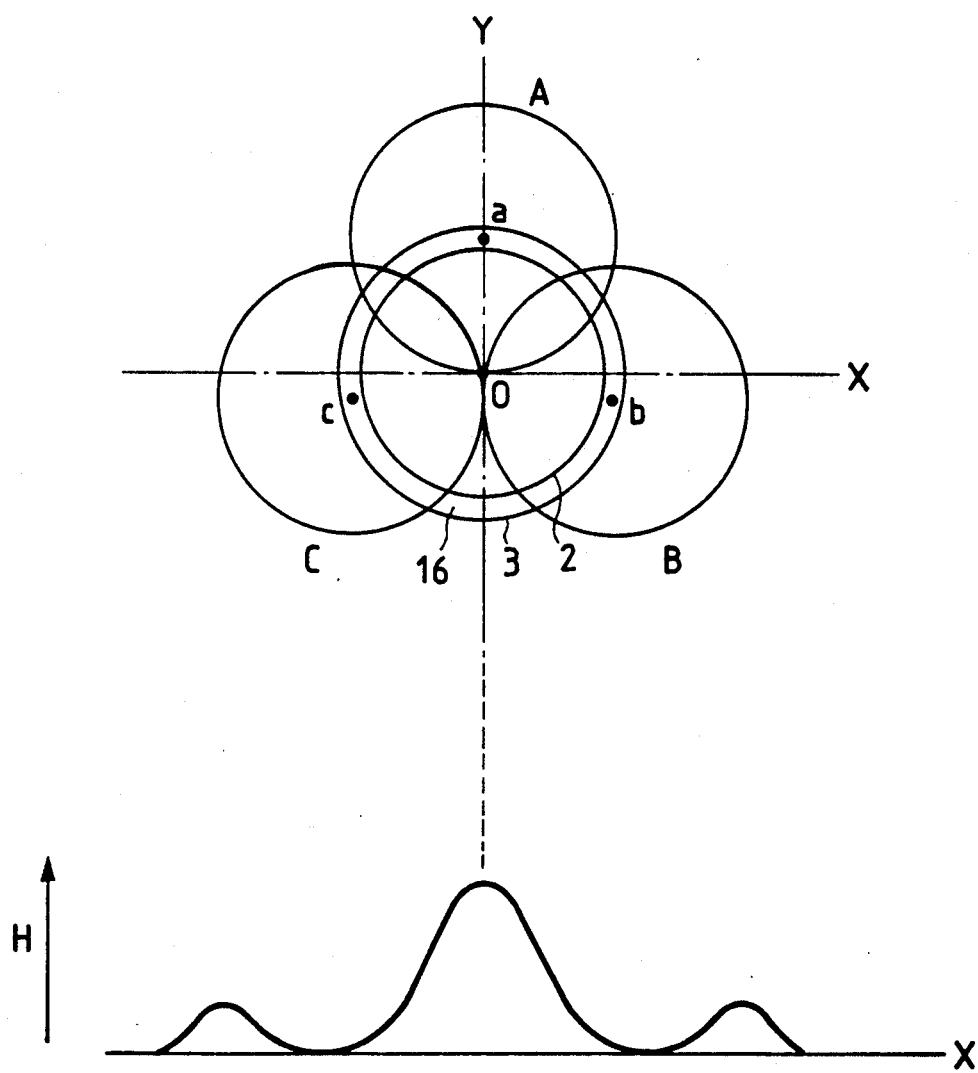
FIG. 3 is a schematic view of an ion distribution in the present invention.

These ions are fed through the hole 8 on the top of the cone shaped convex portion 7 and introduced into the inside of the quadrupole mass filter 9. Some of the ions are reach the detector 10 and the electric signal from the detector 10 according to the ions is amplified by the amplifier 11 and mass spectra are calculated and stored by the data processing system 12. In the next, the nebulizing operation of the ion sprayer of the mass spectrometer shown in FIG. 1 will be explained referring FIG. 3 as follows;

In FIG. 3, numeral 16 denotes a space position between the first inner tube 2 and the second inner tube 3 in the nozzle of the sprayer 1. Circles (A), (B) and (C) denote positions on a XY plane positioned at the hole 8 of the counter electrode. When the liquid sample is ejected from a point (a) of the space 16 in the nozzle, the highest density position of the ions which are ejected from the liquid sample in the point (a) forms the circle (A) on the XY plane. In the same way, when the liquid sample is ejected from a point (b), the highest density position of the ions forms the circle (B) and when the liquid sample is ejected from a point (c), the highest density position of the ions forms the circle (C).

From the relation stated above, when the liquid sample ejected from the space 16, the density H of the ions on the plane becomes as shown in a lower part of the FIG. 3 and the highest density position of the ions is gathered at one point (0) which is overlapped with the circles (A), (B) and (C) and is positioned almost on a central axis of the nozzle having end portions of the first inner tube 2, the second inner tube 3 and the outer tube 4 which are disposed coaxially so as to have the same central axis. The hole 8 of the counter electrode 5 is disposed at the one point (0) which is the highest density position of the ions. Therefore, the ions are most effectively passes through the hole and the sampling efficiency of the ions becomes very high.

In order to gather the highest density position of the ions at the one point(0), other conditions such as a axial position of the first inner tube 2, the second inner tube 3 or the outer tube 4, the flow rate and the temperature of the nebulizing gas or the makeup gas, the voltage applied between the counter electrode 5 and the second inner tube 3 etc. are needed to be controlled suitably.

At least one of the axial position of the first inner tube 2, the second inner tube 3 and the outer tube 4 is manually controlled by a general device not shown the figure so as to keep a suitable distance from the counter electrode 5, and the end portion of the second inner tube 3 is more protruded towards the counter electrode 5 than the ends of the first inner tube 2 and the outer tube 4 in order to obtain the best sampling efficiency.

The flow rates of the nebulizing gas and the makeup gas are easily and respectively controlled by using the control valves 17 and 20 and the temperatures of the nebulizing gas are easily and respectively adjusted by controlling the heaters 16 and 19 in order to obtain the best sampling efficiency.

Figure 4:
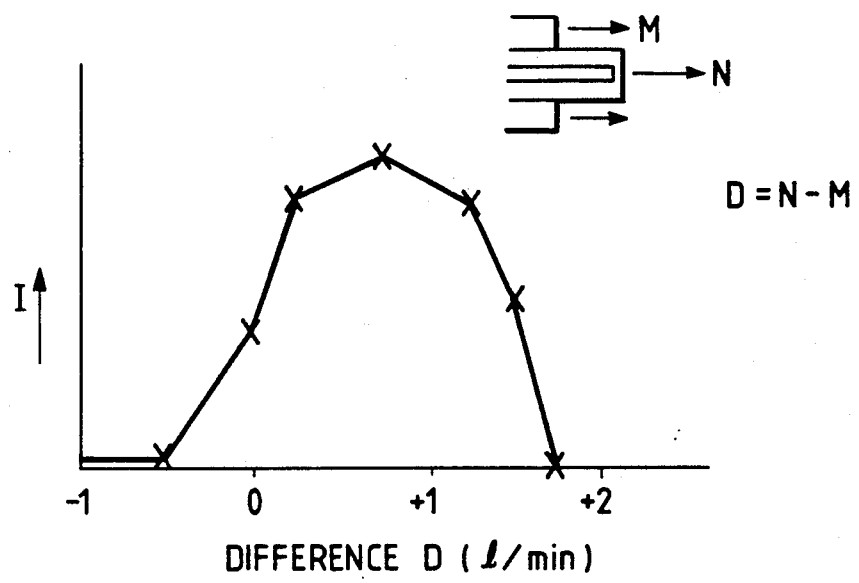
FIG. 4 is a schematic view showing a relation of ion density and a flow rate difference between makeup gas and nebulizing gas in the present invention.

Especially, a relation of the flow rate between the nebulizing gas and the makeup gas is significant in the present invention. FIG. 4 shows the relation of the flow rate and ion current I detected by the detector 10. At this time, ethanol solution(ethanol/water: 80/20) containing ammonium acetate 100 ppm is used as the sample liquid, and the flow rate of the ethanol solution is set to 50 $\mu$l/min. The flow rate of the makeup gas is kept to 1$\mu$/min by the control valve 21. When the flow rate of the nebulizing gas is varied by controlling the control valves 17, ion current I detected by the detector 10 which is proportional to the sampled ions $NH_4$ (m/zl8) is varied like a characteristic curve shown in FIG. 4. The ion current I increases when the flow rate of the nebulizing gas is from 1$\mu$/min to 2.5$\mu$/min, that is, the difference between the nebulizing gas and the makeup gas is from 0 to 1.5$\mu$/min, and the peak of the ion current I appears when the difference between the nebulizing gas and the makeup gas is about 1μ/min. In other words, when ratio of the flow rates between the nebulizing gas and the makeup gas is from 1(the same) to 2.5, the ion current I increases and when the ratio is about 2(twice), the ion current I becomes maximum.

Furthermore, the liquid sample is heated so as to be nebulized effectively. But the liquid sample should not be heated before the sample passes through sprayer 1 because the liquid sample may contain a volatile liquid. Therefore in the present invention, the liquid sample is heated at an outlet position of the nozzle of the sprayer 1 by hot nebulizing gas and hot makeup gas. These hot nebulizing gas and hot makeup gas are respectively obtained from heating by the heaters 17, 20.

Figure 5:
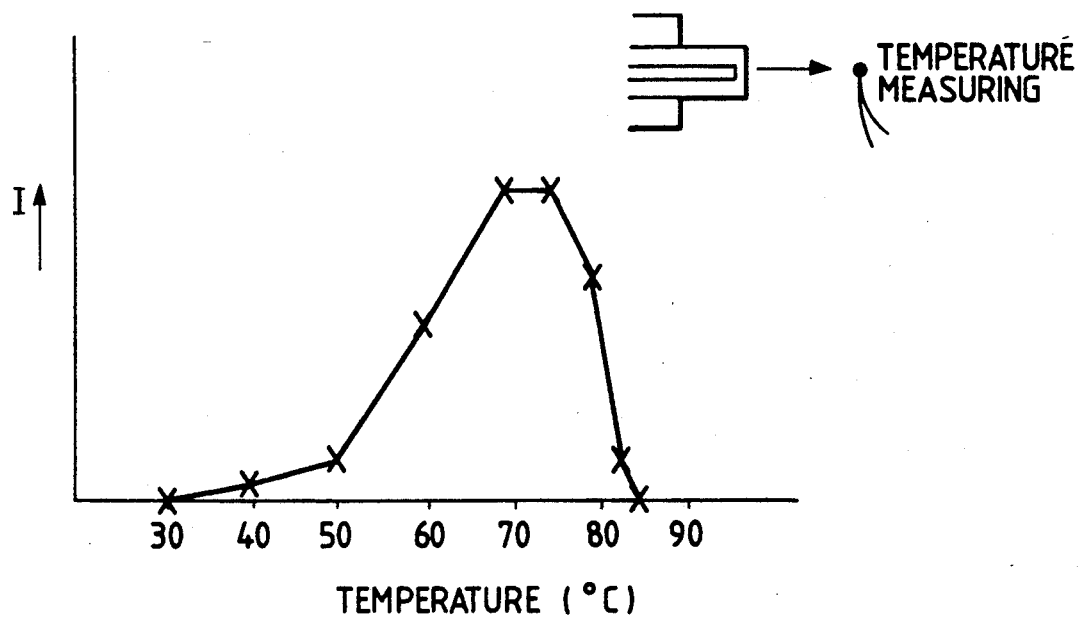
FIG. 5 is a schematic view showing a relation of ion density and a temperature of the makeup gas and the nebulizing gas in the present invention.

FIG. 5 shows a relation between the temperature of the nebulized gas and the makeup gas and the ion current I detected by the detector 10 which is proportional to the sampled ions. When using ethanol solution (ethanol/water: 80/20) containing ammonium acetate 100 ppm as the sample liquid in the same way as in FIG. 4, the suitable temperature of the gases is from 60° C. to 80° C. and the most suitable temperature of the gases at which the ion current I becomes maximum is about 70° C. The ion current I decreases rapidly at 80° C. and becomes zero at 85° C.

Relating to the shape of the counter electrode 5, the convex portion such as a cone which is protruded towards the nozzle of the sprayer is obtained on the counter electrode 5 and the hole 8 is disposed on the top of the convex portion. Such shape cause to effectively induce the ions into the hole by a lens effect of an electrical field generated between the convex portion and the nozzle and a flowing function of the gases.

I claim:

1. A mass spectrometer, comprising
   an ion sprayer having a first tube and a second tube outside of the first tube, wherein nebulizing gas is emitted from the first tube and liquid sample is emitted from a space between the first tube and the second tube,
   a counter electrode for sampling ions having a hole thereon opposite to an outlet of the nebulized gas in the ion sprayer, wherein a high voltage is added between the ion spray device and the electrode so as to sample the ions from the hole,
   a power source for supplying the high voltage, and
   an analyzing means for sorting the masses of the ions sampled through the hole.

2. A mass spectrometer as defined in claim 1, characterized in that
   central axes of the first tube and the second tube are respectively disposed on the same axis.

3. A mass spectrometer as defined in claim 1, characterized in that
   an end portion of the first tube from which the nebulizing gas is emitted is disposed inside of an end of the second tube.

4. A mass spectrometer as defined in claim 1, further comprising
   means for adjusting an axial position of at least one of the first tube and the second tube.

5. A mass spectrometer as defined in claim 1, further comprising
   means for adjusting the flow rate of the nebulizing gas.

6. A mass spectrometer as defined in claim 1, further comprising
   means for adjusting the temperature of the nebulizing gas.

7. A mass spectrometer as defined in claim 6, characterized in that
   said means for adjusting the temperature of the nebulizing gas raises the temperature from 60° C. to 80° C.

8. A mass spectrometer as defined in claim 6, characterized in that
   said means for adjusting the temperature of the nebulizing gas raises the temperature at about 70° C.

9. A mass spectrometer as defined in claim 1, characterized in that
   said hole is disposed on top of a convex portion which is formed on the electrode so as to stand out towards the ion sprayer.

10. A mass spectrometer as defined in claim 1, characterized in that
    said analyzing means comprising a quadrupole mass filter and a detector for detecting the ions passing through the quadrupole mass filter.

11. A mass spectrometer as defined in claim 1, further comprising
    an outer tube outside of the second tube, wherein another gas is emitted from a space between the second tube and the outer tube.

12. A mass spectrometer as defined in claim 11, further comprising
    means for adjusting the flow rate of the other gas.

13. A mass spectrometer as defined in claim 11, further comprising
    means for adjusting the temperature of at least one of the nebulizing gas and the other gas.

14. A mass spectrometer as defined in claim 11, characterized in that
    central axes of the first tube, the second tube and the outer tube are respectively disposed on the same axis.

15. A mass spectrometer as defined in claim 11, characterized in that
    an end portion of the second tube protrudes more than that of the outer tube towards the counter electrode.

16. A mass spectrometer as defined in claim 11, further comprising
    means for adjusting the axial position of at least one of the first tube, the second tube and the outer tube.

17. A mass spectrometer as defined in claim 11, characterized in that
    the ratio of the flow rate of between the nebulizing gas to that of the makeup gas is from 1 to 2.5.

18. A mass spectrometer as defined in claim 11, characterized in that
    the ratio of the flow rate of the nebulizing gas to that of the makeup gas is about 2.

* * * * *